US00PP19011P2

(12) United States Plant Patent
Ault

(10) Patent No.: US PP19,011 P2
(45) Date of Patent: Jul. 8, 2008

(54) *BAPTISIA* PLANT NAMED 'TWILITE'

(50) Latin Name: *Baptisia x variicolor*
Varietal Denomination: Twilite

(75) Inventor: James R. Ault, Libertyville, IL (US)

(73) Assignee: Chicagoland Grows, Glencoe, IL (US)

( * ) Notice: Subject to any disclaimer, the term of this patent is extended or adjusted under 35 U.S.C. 154(b) by 0 days.

(21) Appl. No.: 11/724,126

(22) Filed: Mar. 14, 2007

(51) Int. Cl.
*A01H 5/00* (2006.01)

(52) U.S. Cl. ..... Plt./226
(58) Field of Classification Search ..... Plt./226
See application file for complete search history.

*Primary Examiner*—Kent L. Bell
*Assistant Examiner*—S. B. McCormick Ewoldt
(74) *Attorney, Agent, or Firm*—Penny J. Aguirre

(57) ABSTRACT

A new cultivar of interspecific *Baptisia,* 'Twilite', characterized by its bicolor flowers that are violet-purple with a yellow keel held on erect flower stems, its densely branched, uniform and upright plant habit and its vigorous growth rate.

2 Drawing Sheets

Botanical classification: *Baptisia×variicolor.*
Cultivar designation: 'Twilite'.

BACKGROUND OF THE INVENTION

The present invention relates to a new and distinct cultivar of hybrid *Baptisia* plant, botanically known as *Baptisia× variicolor* 'Twilite' and will be referred to hereafter by its cultivar name, 'Twilite'. The new cultivar represents a new false indigio, an herbaceous perennial grown for landscape use.

The new invention arose from an ongoing controlled breeding program in Glencoe, Ill. There are approximately 17 species of *Baptisia* that are native to North America, many of which have highly ornamental flowers and foliage and excellent adaptability to garden cultivation. The breeding program was established in 1995 with the goal of developing novel interspecific *Baptisia* hybrids with unique and superior garden attributes.

'Twilite' was derived from an F1 cross made in 1998 under controlled conditions (that excluded natural pollinators) between an unnamed plant of *Baptisia australis* as the female parent and an unnamed plant of *Baptisia sphaerocarpa* as the male parent. 'Twilite' was selected in 2002 as a single plant amongst the resulting seedlings and placed under trials for potential introduction.

Asexual reproduction of the new cultivar was first accomplished by stem cuttings in 200 in Glencoe, Ill. by the inventor. The characteristics of this cultivar have been determined to be stable and are reproduced true to type in successive generations.

SUMMARY OF THE INVENTION

The following traits have been repeatedly observed and represent the characteristics of the new cultivar as observed for six years in Glencoe, Ill. These attributes in combination distinguish 'Twilite' from other varieties of *Baptisia* known to the inventor.

1. 'Twilite' exhibits flowers that are bi-color; violet-purple in color with a yellow keel, a characteristics that has not been observed in any species or hybrid known to the inventor.
2. 'Twilite' exhibits blue-green foliage.
3. 'Twilite' exhibits a robust and vigorous growth habit. 'Twilite' is larger and denser than equivalent aged plants of any of the *Baptisia* species or hybrids observed by the inventor.
4. 'Twilite' has an upright and uniform plant habit.
5. 'Twilite' produces abundant flower stems, greater in number than either parent plant.
6. 'Twilite' is hardy to U.S.D.A. Zones 4 to 8.

In comparison to the female parent, *Baptisia austrialis,* 'Twilite' has violet-purple flowers with a yellow keel whereas *Baptisia australis* has blue-violet flowers, 'Twilite' is also more densely branched, more upright, and more uniform. In comparison to the male parent, *Baptisia sphaerocarpa,* 'Twilite' has violet-purple flowers with a yellow keel, blue-green foliage, and grows up to 5 feet in height, whereas *Baptisia sphaerocarpa* has yellow flowers, yellow-green foliage and reaches 2.5 to 3 feet in height. The closest comparison plant is *Baptisia* 'Purple Smoke' (not patented); it is also an interspecific hybrid, however it has violet colored flowers, charcoal gray stems, and is shorter in height than 'Twilite'.

BRIEF DESCRIPTION OF THE DRAWING

The accompanying colored photographs illustrate overall appearance and distinct characteristics of the new *Baptisia.* The photographs were taken of plants and plant parts of a plant six years in age as grown outdoors in Glencoe, Ill.

The photograph in FIG. 1 is a view of a plant of 'Twilite' in bloom and illustrates the dense, uniform habit and the abundance of flowers stems.

Figure 1:
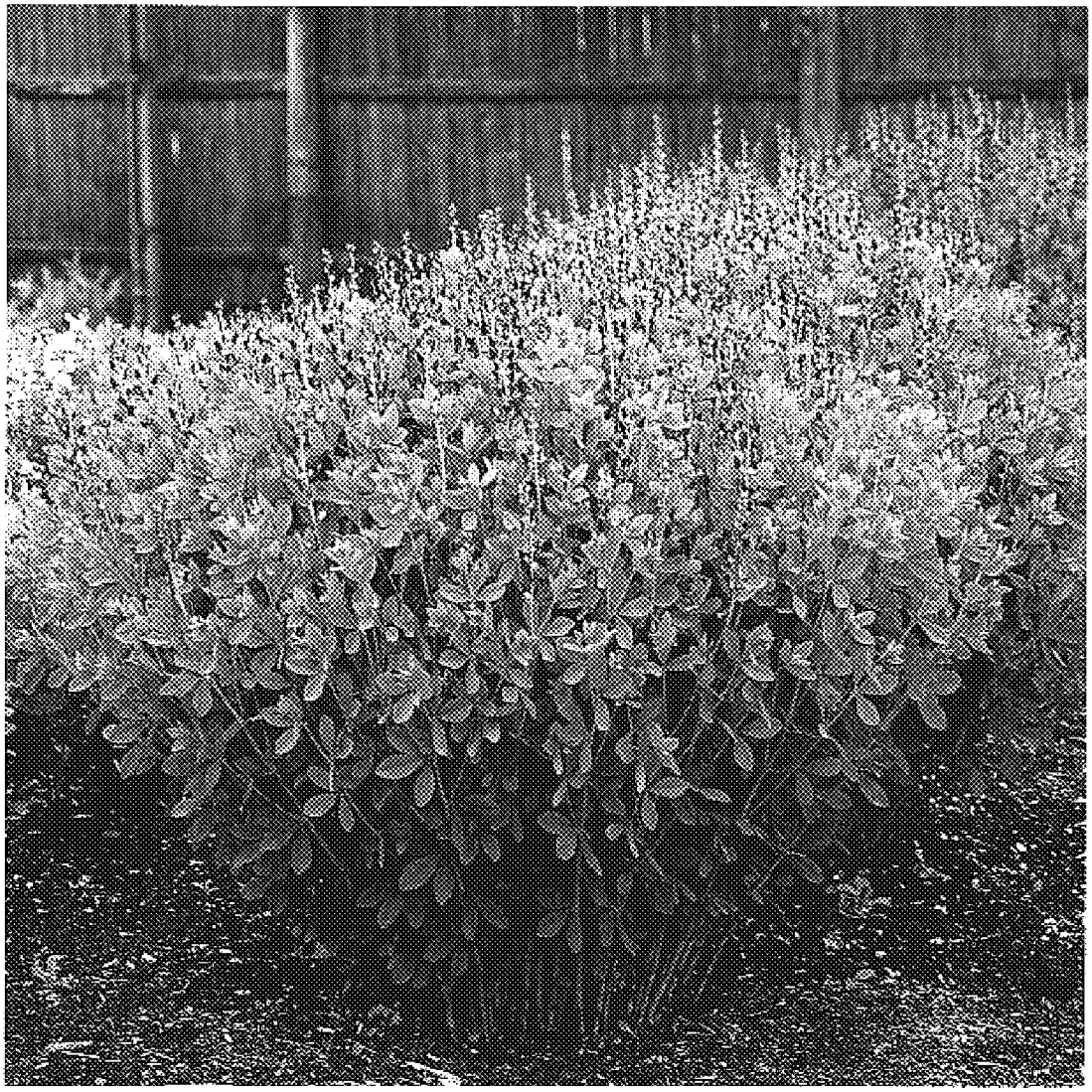
Figure 2:
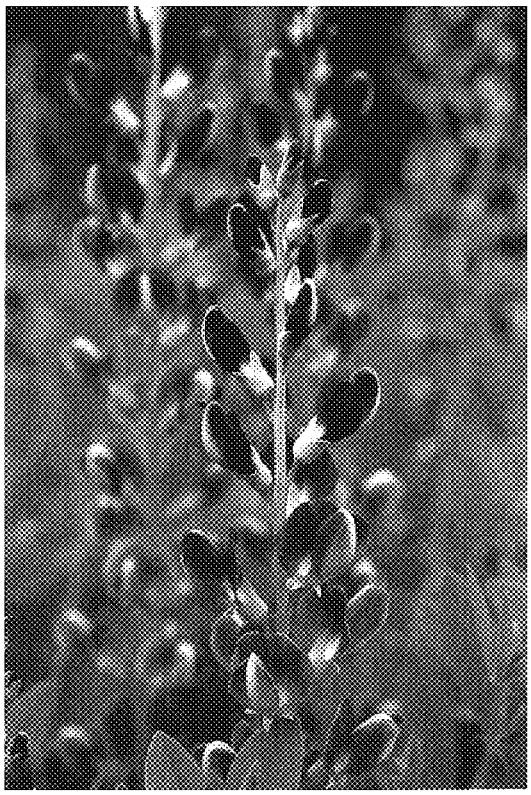

The photograph in FIG. 2 is of a close-up view of the flowers of 'Twilite'.

Figure 3:
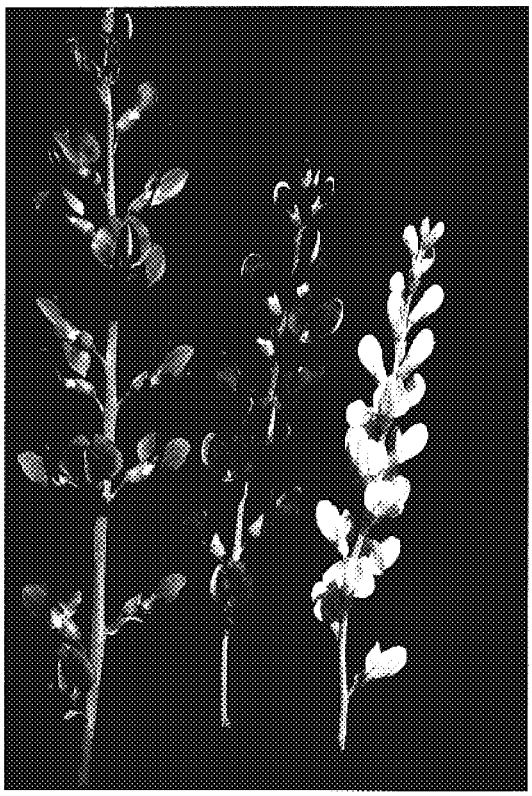

The photograph in FIG. 3 compares flower stems of 'Twilite' with the parent species. 'Twilite' is the center, *Baptisia australis* is on the left, and *Baptisia sphaerocarpa* is on the right.

The colors in the photographs are as close as possible with the photographic and printing technology utilized. The color values cited in the detailed botanical description accurately describe the colors of the new *Baptisia*.

DETAILED BOTANICAL DESCRIPTION OF THE PLANT

The following is a detailed description of 6 year-old plants of the new cultivar as grown outdoors in a trial plot in Glencoe, Ill. The phenotype of the new cultivar may vary with variations in environmental, climatic, and cultural conditions, as it has not been tested under all possible environmental conditions. The color determination is in accordance with the 2001 RHS Colour Chart of The Royal Horticultural Society, London, England, except where general color terms of ordinary dictionary significance are used.

Botanical classification: 'Twilite' is a cultivar of *Baptisia*× *variicolor* (*Baptisia australis*×*Baptisia sphaerocarpa*).

General description:

*Blooming period.*—Late May through mid June in Glencoe, Ill.

*Plant habit.*—Perennial, upright vase-form, uniform, dense.

*Height and spread.*—Reaches 4 to 5 feet in width and up to 5 feet in height.

*Hardiness.*—U.S.D.A. Zones 4 to 8.

*Culture.*—Prefers well-drained to medium moist soils in full sun, tolerant to lean soils and drought.

*Diseases and pests.*—No susceptibility to diseases or pests has been observed.

*Root description.*—Deep rooted, fibrous.

Growth and propagation:

*Propagation.*—Stem cuttings.

*Growth rate.*—Very vigorous relative to other *Baptisia* species and cultivars.

Stem description:

*Branch habit.*—Densely branched; average of 3 primary branches, typically 2 to 3 secondary branches, and 1 to 3 tertiary branches.

*Stem size.*—Reaches up to 1.5 m (5 feet) in length, average of 6 to 7 mm in width.

*Stem shape.*—Oval.

*Stem color.*—144A to 144B.

*Stem surface.*—Hairless, satiny but slightly glaucous, finely ribbed.

Foliage description:

*Leaf shape.*—Fan-shaped in overall outline.

*Leaf division.*—3-palmate.

*Leaf internode.*—Varies from about 15 to 18 cm from base of laterals branch to 3 to 8 cm on tertiary branches.

*Leaf size.*—About 4 to 6 cm in length and 4 to 7 cm in width when mature.

*Leaf quantity.*—About 15 to 20 per lateral branch.

*Leaflet shape.*—Oblanceolate.

*Leaflet base.*—Cuneate, almost attenuate.

*Leaflet apex.*—Acute to rounded.

*Leaflet venation.*—Pinnate pattern, not conspicuous, color matches leaflet color on the upper and lower surface with the mid rib of lower surface 144A.

*Leaflet margins.*—Entire.

*Leaf attachment.*—Petiolate.

*Leaf arrangement.*—Alternate.

*Leaflet surface.*—Glaucous on upper and lower surface.

*Leaflet color.*—Newly expanded; upper and lower surface 144A, mature: upper; and lower surface 137A.

*Leaflet size.*—Up to about 7 cm in length, up to about 2.5 cm in width.

*Petioles.*—Average of 4 mm in length and 2.5 mm in width, clasping to stem at mature nodes, 144A in color, surface is hairless and satiny.

*Stipules.*—Lanceolate in shape, base is truncate to stem, apex is narrowly acute to acuminate, average of 1.5 cm in length and 5 mm in width but varies from minute newly formed leaves to 3.5 cm in length and 1 cm in width on basal nodes, 137A in color on upper and lower surface.

Flower description:

*Inflorescence type.*—Terminal and auxiliary racemes of bi-color pea-like flowers, blooms from the base to apex.

*Inflorescence size.*—Up to 50 cm in length and 4.5 cm in width.

*Lastingness of inflorescence.*—3 to 4 weeks.

*Flower size.*—About 2.5 cm in depth and about 2 cm in diameter.

*Flower fragrance.*—None.

*Flower number.*—About 35 to 40 on terminals, about 15 to 25 on auxiliary branches.

*Peduncle.*—Oval in shape, up to 50 cm in length and ranges from 5 cm in width at the base of the inflorescence to 2 mm in width at the apex, 144A to 144B in color, surface is hairless, satiny but slightly glaucous and finely ribbed, flower internode length ranges from 5 mm to 4 cm with an average of 1 cm.

*Petiole.*—About 5 mm in length, about 1.5 mm in width, oval in shape, 144A in color, satiny surface.

*Flower buds.*—Kidney shaped, about 2 cm in length and 8 mm in width, bicolor; visually 83A in center with a margin of 150C, calyx portion same as open flowers.

*Flower type.*—Papilionaceous, held at about 45° C. angle.

*Calyx.*—Campanulate, about 7 mm in length and 6 mm in diameter, surface is slightly glaucous, 144B in color with a few flecks of N79A, persistent.

*Sepals.*—5, fused with the exception of apex of each, free portion is triangular in shape 4 mm in width and 3 mm in depth with an acute apex, 144B in color with a few flecks of N79A.

*Corolla features.*—Papilionaceous (4 segments) with a keel, an inner lip and 2 lateral wings, the inner lip; comprised of two lobes that are folded around stamens and pistil, lobes are reniform in shape, about 1.3 cm in length and 8 mm in width, lower ⅔ is 2D in color and upper ⅓ is 83A in color on outer surface and the inner surface is 2D flushed with 83A at the apex, rounded apex, lateral wings; loosely surround inner lip, oblong in shape, about 2 cm in length and 8 mm in width, upper and lower surface is 83A in color with a base of 2D, rounded apex, keel; reflexed, orbicular in shape with cordate apex, 1.8 mm in length and width, upper surface and lower surface are 83A in color with a base of 2D, all segments; glabrous in texture, entire margin. base is rounded with a short attenuated section on keel and oblique with an attenuated section on other segments.

*Receptacle.*—Disk-shaped, gelatinous, 144A in color, about 3 mm in diameter and 1.2 mm in depth.

Reproductive organs:

*Gynoecium.*—1 Pistil, about 1.8 mm in length, 1 mm in width; style is 138D in color; stigma minute, too small to color read; Ovary is superior with a stipe, 138B in color, 6 mm in length and 1 mm in width; stipe is 138D in color, 3 mm in length and <1 mm in width.

*Androecium.*—10 stamens, not united, 2 mm in length and 1 mm in width; filament is 1.9 cm in length, 1 mm in width and 138D in color; anther is dorsifixed, 1 mm in length, <1 mm in width and 22 A in color, pollen is abundant and 15A in color.

*Fruit.*—An inflated pod, technically a legume, 25 to 30 produced per inflorescence (open-pollinated), globose-oblongoid in shape, 25 to 35 mm in length by 15 to 20 mm in width; each with a short beak approx. 5 mm in length, emerges green and matures in August to charcoal black outside (between 201A and 202A), tan inside, walls thick (3 mm) and woody at maturity. Seed 6 to 12 per fruit (open-pollinated), light to medium brown (164D to 165A), oval with the hilum side more or less straight, seed compressed to flattish, 4 mm long×3 mm wide×1.5 mm thick.

I claim:

1. A new and distinct cultivar of *Baptisia* plant named 'Twilite' as herein illustrated and described.

* * * * *